US012605496B2

(12) United States Patent
Srisailappa Gopasetty

(10) Patent No.: US 12,605,496 B2
(45) Date of Patent: Apr. 21, 2026

(54) BIOENGINEERED ARTIFICIAL LATERAL LIVER (BALL) OR BIOENGINEERED ARTIFICIAL ECTOPIC LIVER (BAEL)

(71) Applicant: Ykrita Lifesciences Private Limited, Bangalore (IN)

(72) Inventor: Mahesh Srisailappa Gopasetty, Bangalore (IN)

( * ) Notice: Subject to any disclaimer, the term of this patent is extended or adjusted under 35 U.S.C. 154(b) by 660 days.

(21) Appl. No.: 17/641,096

(22) PCT Filed: Jun. 24, 2021

(86) PCT No.: PCT/IN2021/050614
§ 371 (c)(1),
(2) Date: Mar. 8, 2022

(87) PCT Pub. No.: WO2021/260735
PCT Pub. Date: Dec. 30, 2021

(65) Prior Publication Data
US 2022/0331502 A1 Oct. 20, 2022

(30) Foreign Application Priority Data
Jun. 26, 2020 (IN) .............................. 202041027148

(51) Int. Cl.
*A61M 1/34* (2006.01)
*C12M 1/12* (2006.01)
*C12N 5/071* (2010.01)

(52) U.S. Cl.
CPC ......... *A61M 1/3489* (2014.02); *C12N 5/0671* (2013.01); *A61M 2205/0244* (2013.01)

(58) Field of Classification Search
CPC ........ A61M 1/3489; A61M 2205/0244; A61M 2207/00; A61M 1/34; A61M 1/16;
(Continued)

(56) References Cited

U.S. PATENT DOCUMENTS 5,976,870 A * 11/1999 Park .................... A61M 1/3472
435/395
6,294,380 B1 * 9/2001 Qiang ................. A61M 1/3687
435/395
(Continued)

FOREIGN PATENT DOCUMENTS

EP 2900801 A1 8/2015
KR 102101060 B1 4/2020
WO 2020155909 A1 8/2020

OTHER PUBLICATIONS

Lab Chip, 2015, 15, 3822. (Year: 2015).*

*Primary Examiner* — Pranav N Patel
(74) *Attorney, Agent, or Firm* — Prakash Nama; Global IP Services, PLLC

(57) ABSTRACT

The embodiments provide a bioengineered artificial functional liver which is connected to a patient suffering from acute liver failure and would functional like an ectopic liver. The device uses the cells derived from the patient's own body thereby nullifying the chances of self/non-self-recognition and related immune activation and rejection. The extracted liver cells are grown on a customized 3D matrix called as 3D cell cartridge and these cell cartridges individually function as miniature liver assemblies. Multiple such assemblies when working in parallel would rescue the condition of liver failure. A microfluidic chamber is built with the similar network as found in the liver and the chamber has flow circuits for plasma/de-cellularised blood and the flow circuits are lined by a coculture of hepatocytes, endothelial cells and fibroblasts. The array of cells in the chamber serve as a miniature liver and multiple such arrays will be stacked to achieve a significant hepatic function.

5 Claims, 6 Drawing Sheets

(58) Field of Classification Search
CPC ...... C12N 5/0671; C12N 5/071; C12N 15/10;
C12M 25/04; C12M 35/08; C12M 3/06;
C12M 1/14; C12M 1/40; B01D 61/14;
B01D 61/18; B01D 61/24; B01D 63/08
See application file for complete search history.

(56) References Cited

U.S. PATENT DOCUMENTS

| | | | |
|---|---|---|---|
| 2013/0236972 A1* | 9/2013 | Noh ....................... | C12N 5/067 |
| | | | 435/401 |
| 2014/0289877 A1* | 9/2014 | Taniguchi ........... | A61L 27/3804 |
| | | | 435/1.1 |
| 2017/0252500 A1* | 9/2017 | Kumar ................... | C12M 23/34 |
| 2019/0093077 A1* | 3/2019 | Hamilton ............... | C12N 5/067 |
| 2020/0061276 A1* | 2/2020 | Yonemitsu ............. | C12M 23/44 |
| 2021/0176981 A1* | 6/2021 | Correns ................ | A01M 29/00 |
| 2021/0176984 A1* | 6/2021 | Paun ..................... | C12M 29/04 |
| 2021/0292714 A1* | 9/2021 | Takebe ................... | C12M 25/14 |

* cited by examiner

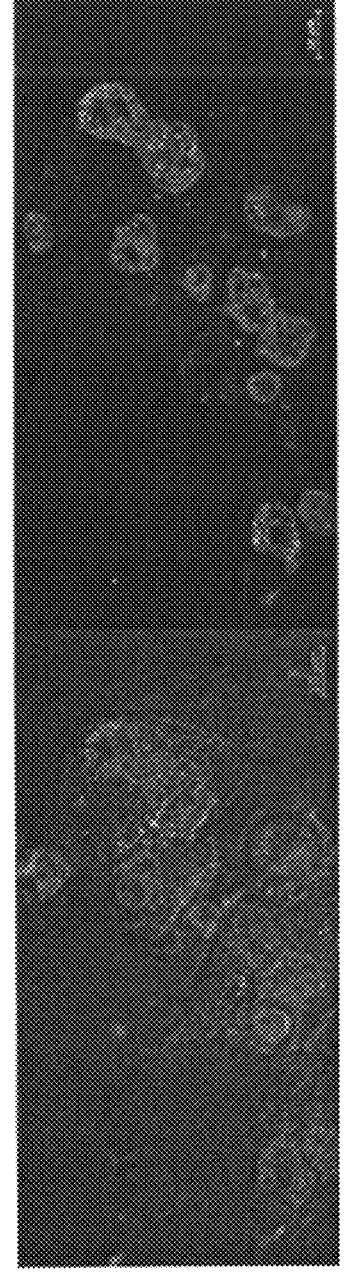
MRP 2-Red DAPI - Blue
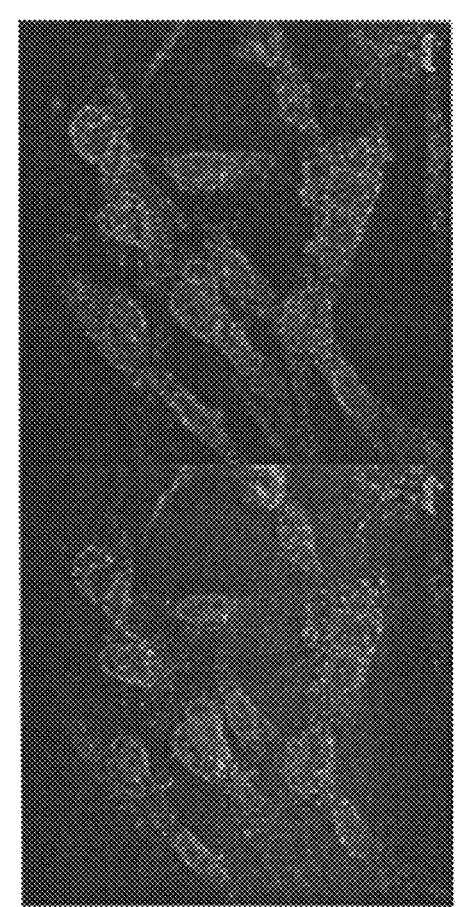
ZO-1-Red DAPI - Blue
FIG. 02

ALBUMIN DAY 7

ALBUMIN DAY 14

ALBUMIN DAY 6

ALBUMIN DAY 10

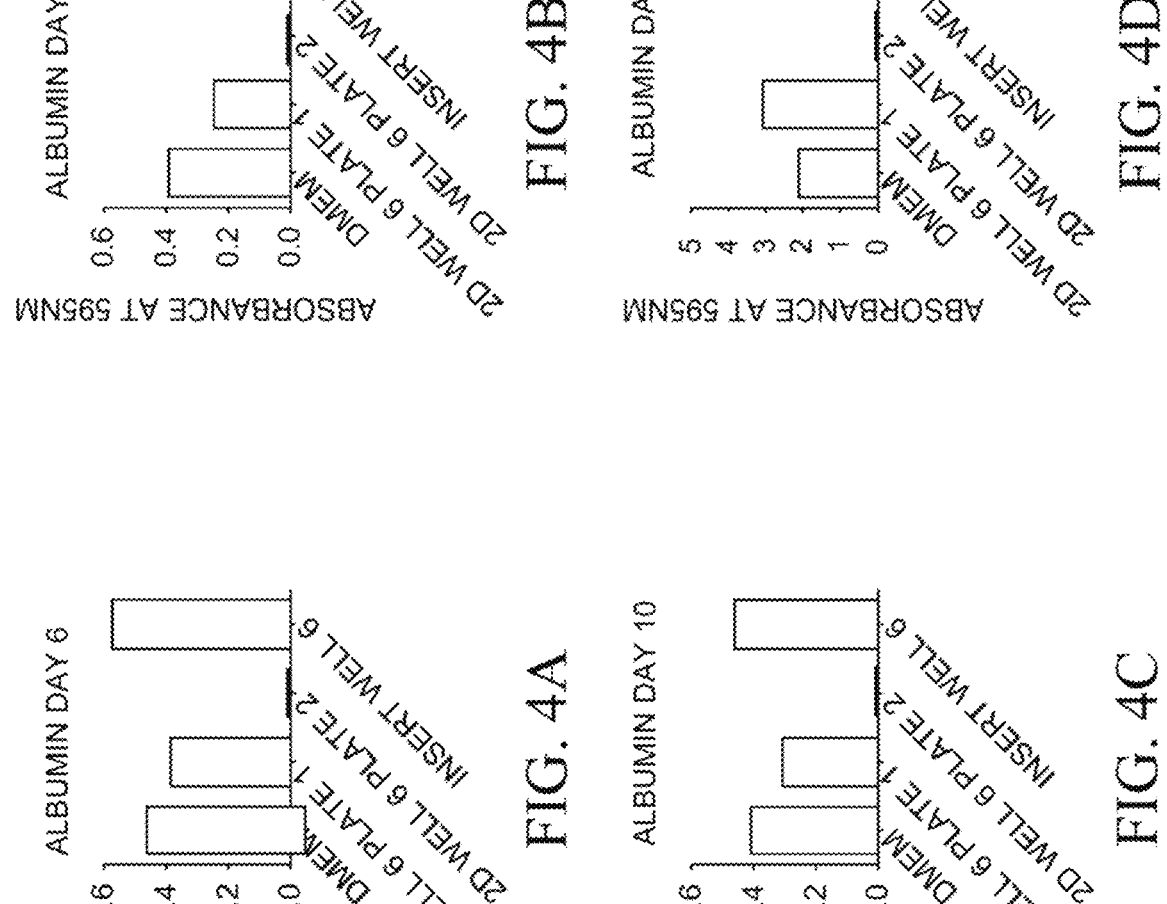

BIOENGINEERED ARTIFICIAL LATERAL LIVER (BALL) OR BIOENGINEERED ARTIFICIAL ECTOPIC LIVER (BAEL)

A) CROSS-REFERENCE TO RELATED APPLICATION

This application claims the priority from the Provisional Patent Application filed at the Indian Patent Office dated 26 Jun. 2020 bearing the Indian Patent Application Number 202041027148 and titled, "BIOENGINEERED ARTIFICIAL LATERAL LIVER (BALL) OR BIOENGINEERED ARTIFICIAL ECTOPIC LIVER (BAEL)", each of which is hereby incorporated by reference herein for all purposes.

B) TECHNICAL FIELD

The present invention generally relates to healthcare and biomedical devices. More particularly, the present invention is aimed at providing a Bioengineered Artificial Ectopic Liver (BAEL) device which uses the biologically active cells that are grown on a 3D matrix and wherein the Bioengineered Artificial Ectopic Liver (BAEL) device can be externally connected to the patient's body directly into the blood stream.

C) BACKGROUND OF THE INVENTION

Acute liver failure (ALF) is a life-threatening illness, where a previously normal liver fails within days to weeks. Sudden loss of synthetic and detoxification function of liver results in jaundice, encephalopathy, coagulopathy, and multiorgan failure. The etiology of ALF varies demographically. In India, Acute viral hepatitis is the most common cause of ALF. The mortality of ALF is as high as 40-50% and causes of death in ALF include brain herniation due to raised intracranial pressure (35%) and sepsis with multi-organ failure. Liver transplantation remains the only therapeutic intervention with proven survival benefit in patients with irreversible ALF.

Acute liver failure occurs when liver cells are damaged significantly and are no longer able to function. Potential causes include:
- a. Acetaminophen overdose. Taking too much acetaminophen (Tylenol, others) is the most common cause of acute liver failure in the United States. Acute liver failure can occur after one very large dose of acetaminophen, or after higher than recommended doses every day for several days.
- b. Prescription medications. Some prescription medications, including antibiotics, nonsteroidal anti-inflammatory drugs and anticonvulsants, can cause acute liver failure.
- c. Herbal supplements. Herbal drugs and supplements, including kava, ephedra, skullcap and pennyroyal, have been linked to acute liver failure.
- d. Toxins. Toxins that can cause acute liver failure include the poisonous wild mushroom *Amanita phalloides*, which is sometimes mistaken for one that is safe to eat. Carbon tetrachloride is another toxin that can cause acute liver failure. It is an industrial chemical found in refrigerants and solvents for waxes, varnishes and other materials.
- e. Autoimmune disease. Liver failure can be caused by autoimmune hepatitis—a disease in which your immune system attacks liver cells, causing inflammation and injury.

- f. Diseases of the veins in the liver. Vascular diseases, such as Budd-Chiari syndrome, can cause blockages in the veins of the liver and lead to acute liver failure.
- g. Metabolic disease. Rare metabolic diseases, such as Wilson's disease and acute fatty liver of pregnancy, infrequently cause acute liver failure.
- h. Cancer. Cancer that either begins in or spreads to your liver can cause your liver to fail.
- i. Shock. Overwhelming infection (sepsis) and shock can severely impair blood flow to the liver, causing liver failure.
- j. Many cases of acute liver failure have no apparent cause.
- k. People with acute liver failure are often treated in the intensive care unit of a hospital in a facility that can perform a liver transplant, if necessary. Doctor may try to treat the liver damage itself, but in many cases, treatment involves controlling complications and giving liver time to heal.

Further to this, treatments to acute liver failure includes:
- a. Medications to reverse poisoning. Acute liver failure caused by acetaminophen overdose is treated with a medication called acetylcysteine. This medication may also help treat other causes of acute liver failure. Mushroom and other poisonings also may be treated with drugs that can reverse the effects of the toxin and may reduce liver damage.
- b. Liver transplant. When acute liver failure can't be reversed, the only treatment may be a liver transplant. During a liver transplant, a surgeon removes your damaged liver and replaces it with a healthy liver from a donor.
- c. Relieving pressure caused by excess fluid in the brain. Cerebral edema caused by acute liver failure can increase pressure on the brain. Medications can help reduce the fluid build-up in brain.
- d. Screening for infections & Preventing severe bleeding.

Currently, orthotopic liver transplantation (OLT) remains the only definite therapy for patients with irreversible liver injury. With OLT, the overall survival of ALF has improved to 60%. The majority of deaths occurs within 3 months of transplant and is due to neurologic complications or sepsis. Living-related liver transplant (LDLT) is common in Asia. For ALF, LDLT may reduce waiting time and provide better timing compared to deceased donor liver transplantation. Recent data from Asia with right lobe LDLT have shown improved survival of adult patients with ALF. ABO incompatible grafts are increasingly being used in acute settings. ABO incompatible grafts have a less favorable outcome with 30-60% 1-year survival. Auxiliary liver transplant retains recipient liver and uses a partial right or left lobe of donor liver as a temporary liver support. Once the native liver recovers immunosuppression is gradually withdrawn and donor liver shrinks. Overall survival for auxiliary liver transplant is 60-65%. Artificial and bioartificial liver (BAL) support systems are intended to support the patient till his or her liver regenerates or till liver transplantation is available. Artificial liver support systems are filtration and adsorption devices that remove accumulated toxins from the blood.

In addition to the removal of water-soluble substances, these systems remove lipophilic albumin-bound substances such as bilirubin, bile acids, medium chain fatty acids, metabolites of aromatic amino acids, and cytokines. BAL combines detoxification with synthetic and regulatory function of hepatocytes. Such systems are not very effective in the clinical setting as the natural functions of hepatocytes are not restores. In prolonged treatments, the body also starts showing resistance to such devices and therefore the efficiency of these devices is not fool-proof.

Hence, in view of the foregoing, there is a need to provide an effective device, which works as an artificial human liver that is cost effective, and provide similar biochemical functionalities of a natural human liver.

The above-mentioned shortcomings, disadvantages and problems are addressed herein, which will be understood by reading the following specification.

D) OBJECTS OF THE INVENTION

The primary object of the present invention is to provide a bioengineered artificial functional liver which can be connected to a patient suffering from acute liver failure.

The other object of the present invention is to provide a 3D cell cartridge which will use biologically active cells, capable of performing detoxification functions, such that the 3D cell cartridge functions as human liver in cleansing the impurities in the blood stream.

Another object of the present invention is to provide the development of portable device in which an in-line plasma separator and a 3D cell matrix together function the process of pumping the blood, separating the plasma of the blood stream, cleanse the impurities in the blood with the 3D cell matrix and pump back the blood to the human body thereby performing a function of a liver.

These and other objects and advantages of the present invention will become readily apparent from the following detailed description taken in conjunction with the accompanying drawings.

E) SUMMARY OF THE INVENTION

The embodiments of the present invention provide a bioengineered artificial functional liver which can be connected to a patient suffering from acute liver failure.

According to the embodiment, the engineered implantable device, which would functional like an ectopic liver. The device uses cells which cannot trigger an immune response thereby nullifying the chances of self/non-self-recognition and related immune activation and rejection. Here the cells are grown on a customized 3D matrix called as 3D cell cartridge.

According to the embodiment, these 3D cell cartridges individually function as miniature liver assemblies. Multiple such assemblies when working in parallel would rescue the condition of liver failure.

According to the embodiment, the engineered implantable device can be used as an external attachment to the patient. This device will function like a live native liver. This external device will allow the damaged liver to regenerate by reducing the metabolic burden.

According to the embodiment, a microfluidic chamber is built with the similar network as found in the liver. This chamber has flow circuits for plasma/de-cellularised blood. The flow circuits are lined by a coculture of cells. This co-culture combination has been developed by us in the preliminary stages of the project. The array of cells in the chamber serve as a miniature liver. Multiple such arrays will be stacked to achieve a significant hepatic function.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

F) BRIEF DESCRIPTION OF THE DRAWINGS

The other objects, features and advantages will occur to those skilled in the art from the following description of the preferred embodiment and the accompanying drawings in which:

FIG. 2 illustrates the establishment of co-culture wherein MRP2 and ZO-1 are markers for cell polarization and DAPI is a nuclear marker according to an embodiment of the present invention.

FIG. 4 illustrates the functional validation of the 3D cell culture setup under conditions of continuous flow by albumin measurements according to an embodiment of the present invention.

Figure 1:
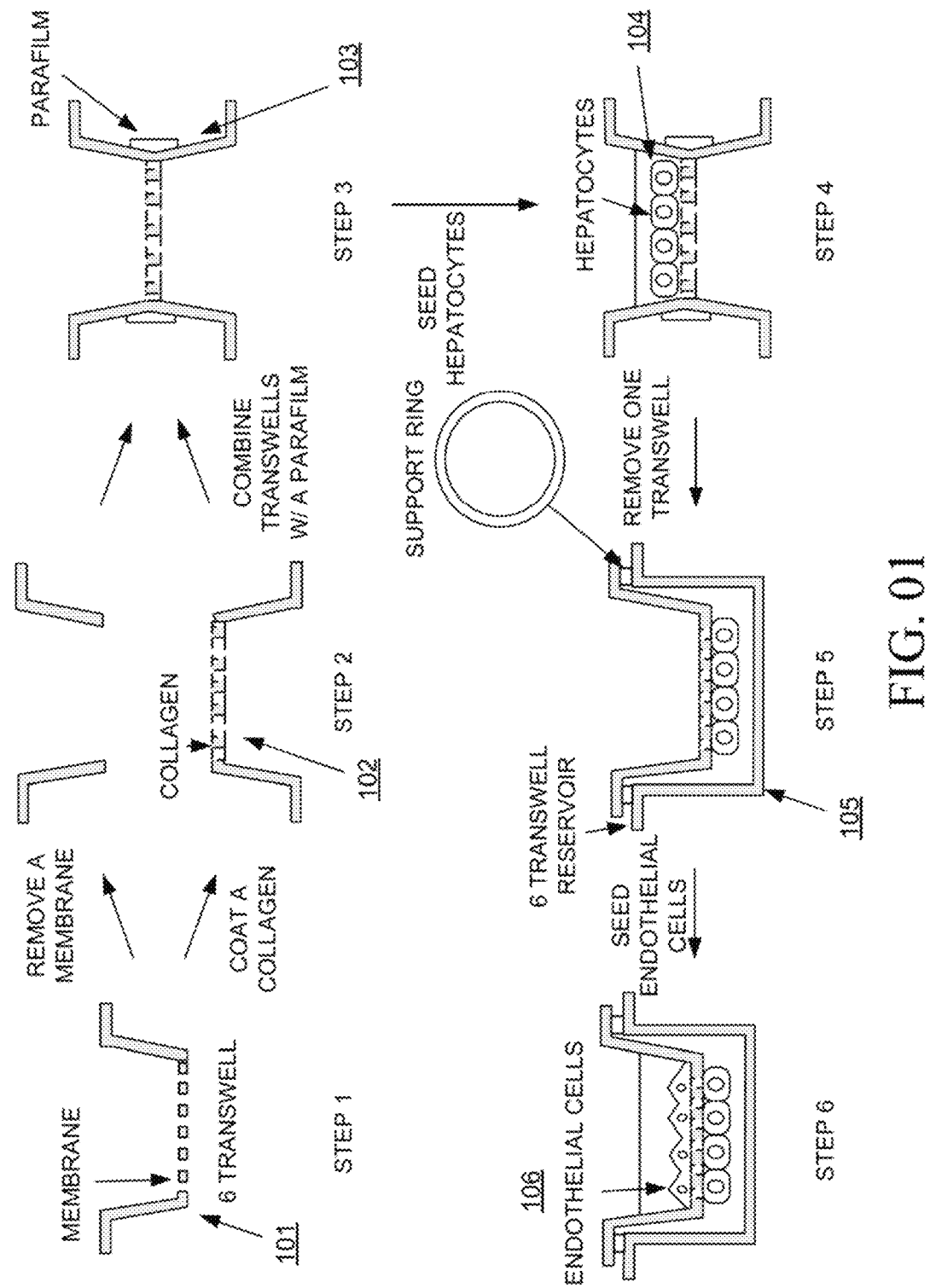
FIG. 1 illustrates a schematic of the 3D culture set-up for cell culture according to an embodiment of the present invention.
Figure 3B:
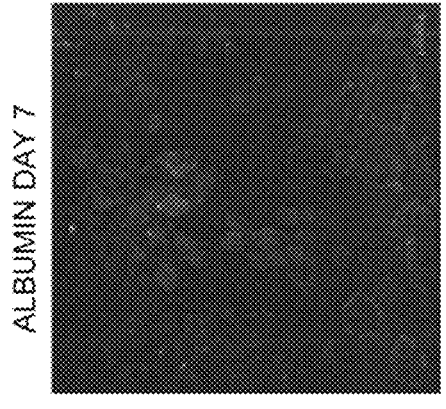
FIG. 3 illustrates the status of cell co-culture after 14 days wherein the staining reflects that the cells are viable according to an embodiment of the present invention.
Figure 3D:
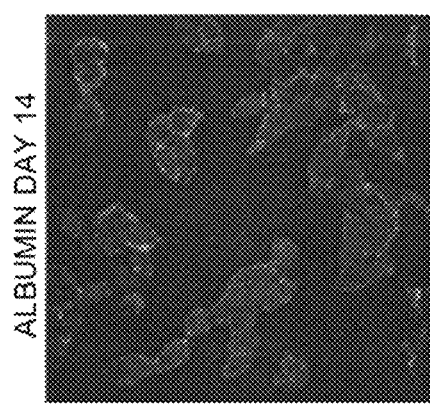
Figure 3A:
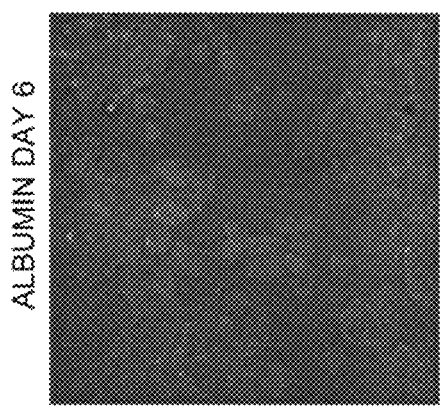
Figure 3C:
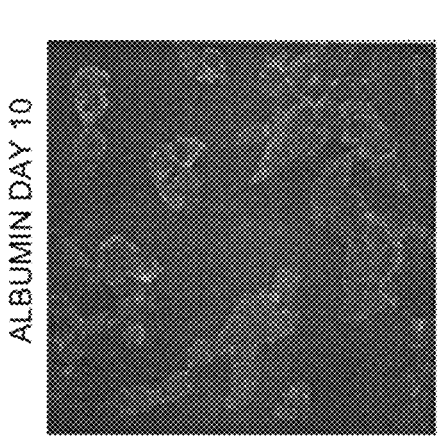

Although specific features of the present invention are shown in some drawings and not in others. This is done for convenience only as each feature may be combined with any or all of the other features in accordance with the present invention.

G) DETAILED DESCRIPTION OF THE INVENTION

In the following detailed description, reference is made to the accompanying drawings that form a part hereof, and in which the specific embodiments that may be practiced is shown by way of illustration. These embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The present invention discloses an engineered implantable device, which would functional like an ectopic liver. The device uses immunologically neutral cells thereby nullifying the chances of self/non-self-recognition and related immune activation and rejection. Here the cells are grown on a customized 3D matrix called as 3D cell cartridge. These cell cartridges individually function as miniature liver assemblies. Multiple such assemblies when working in parallel would rescue the condition of liver failure. As opposed to transplanting liver, which have serious disadvantages, the ectopic liver would be an alternative strategy to provide hepatic functioning in cases of ALF. This device can be used as an external attachment to the patient. This device will function like a live native liver. This external device will allow the damaged liver to regenerate by reducing the metabolic burden.

Accordingly, a microfluidic chamber is built with the similar network as found in the liver. This chamber has flow circuits for plasma/de-cellularised blood. The flow circuits are lined by a coculture of cells. This co-culture combination has been developed by us in the preliminary stages of the project. The array of cells in the chamber serve as a miniature liver. Multiple such arrays will be stacked to achieve a significant hepatic function. We have also co-cultured these cells of relevance on either side of a 3D construct and maintained them using complete medium resembling plasma for about 30 days. The material used for growing the 3D culture was uniquely identified by us. The culture was monitored for viability and functioning for this period. Systematic analysis of the cell proliferation, albumin production and cell polarization has been done. The data in support of this is included in the later part of this report. It was found that, during this time they functioned well and did all the functions of liver better than the cells maintained in a 2D culture set-up. We chose plasma to blood to maintain the cells, because WBC form part of the blood which identify foreign cells and destroy them. We believe that by using plasma, we will be avoiding this problem of destruction and sensitization.

In our proposed device, there are 2 innovative concepts. 1$^{st}$ is the use of a 3D cell cartridge which will use metabolically active cells which are capable of performing detoxification processes. 2$^{nd}$ innovative concept is the development of an in-line plasma separator. Both the 2 concepts when put together, make up a functional liver-like device which can be connected to a patient suffering from acute liver failure. Hence, we claim the design of a bioengineered artificial liver. This invention is the first of its own kind which has a potential to disrupt the existing treatment modalities related to liver failure and transplant.

FIG.1 illustrates a schematic of the 3D culture set-up for culturing cells on a single membrane according to an embodiment of the present invention. At 101 (e.g. step 1), the membrane for the cell culture is customized as per the need and is made of Polycarbonate material with a pore size of at least 0.4 microns. An example membrane is a 6 transwell membrane. At 102 (e.g. step 2), the 6 transwell membrane which is commonly used in culturing of cells on a membrane is used by removing an existing membrane and applying a coating of collagen over a new membrane. At 103 (e.g. step 3), the removed membrane is replaced by combining 6 transwells membrane with a parafilm. The membrane (101) has two surfaces on which one side biologically active cells A (e.g. hepatocytes cells) and on the other surface biologically active cells B (e.g., endothelial cells) are cultured (which is a 3D cell cartridge). Once the 6 transwells are combined with the parafilm, at 104 (e.g. step 4), biologically active hepatocytes cells are cultured on one surface of the 6 transwell membrane. At 105 (e.g., step 5), one of the 6 transwell is removed and 6 transwell reservoir is created using a support ring. The 6 transwell reservoirs are filled with tissue culture medium which supports the growth of the biologically active hepatocytes cells. At 106 (e.g., step 6), endothelial cells which are biologically active cells derived from the patient's plasma are seeded and cultured over this vacant membrane collagen and filled with the tissue culture medium. Precisely, the 3D cell culture setup comprises of a customized membrane with appropriate coating. Cell A and Cell B are layered on the membrane sequentially and the setup is incubated in 37-degree Celsius incubator for attachment. Upon successful attachment of the cells to the membrane, the reservoirs are filled with tissue culture medium which supports the growth of the biologically active cells.

Further, the ratio of the cell number is kept at optimal (Cell A: Cell B) which is cultured herein. Hence, this new process allows the growth of two biologically active cells on a single 6 membrane which are used in a 3D cartridge in the bioartificial liver device for removing lipophilic albumin-bound substances such as bilirubin, bile acids, medium chain fatty acids, metabolites of aromatic amino acids, and cytokines from the patient's blood.

FIG. 2 illustrates the establishment of co-culture wherein markers for cell viability and nucleus are used according to an embodiment of the present invention. Accordingly, once the cell culturing process has started on the membrane we need examine and track the state (alive or dead) and growth progress of these biological active cells. The validation of the cell growth is shown in the FIG. 2 at the zero hour.

FIGS. 3A-3D illustrate the status of cellular co-culture after 14 days wherein the staining reflects that the cells are viable according to an embodiment of the present invention. Accordingly, the validation of the cell growth is shown in the FIG.3 at the 14th day. For the cell to be cultured and used in the 3D cartridge it requires 14 complete days for culturing the biologically active cells.

FIGS. 4A-4D illustrate the functional validation of the 3D cell culture setup by albumin measurements observed over 14 days according to an embodiment of the present invention. The effectiveness of the cultured 3D cell is measured by albumin measurements. The legend marked with "well 6" (the last purple bar) indicates its effectiveness of being fully functional even at day 14. The legend marked with "DMEM" is culture medium used for growing cells. Hence, this measurement proves that cultured cell in the 3D cell cartridge is healthy and active even on day 14.

Figure 5:
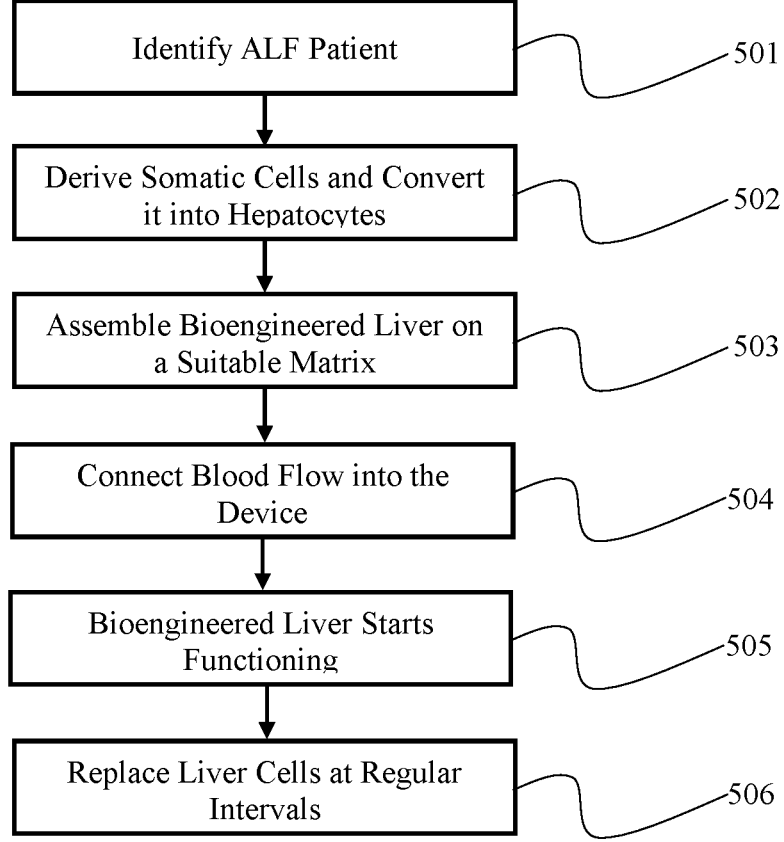
FIG. 5 is an example method for connecting a bioengineered artificial functional liver device to a patient suffering from acute liver failure.

FIG. 5 is an example method for connecting a bioengineered artificial functional liver device to a patient suffering from acute liver failure. At 501, acute liver failure (ALF) patient is identified. At 502, somatic cells are derived and converted into hepatocytes. At 503, the bioengineered artificial functional liver device is assembled on a suitable matrix. At 504, the blood flow is connected into the device. At 505, the functioning of the bioengineered artificial functional liver device is started. At 506, liver cells are replaced at regular intervals.

Figure 6:
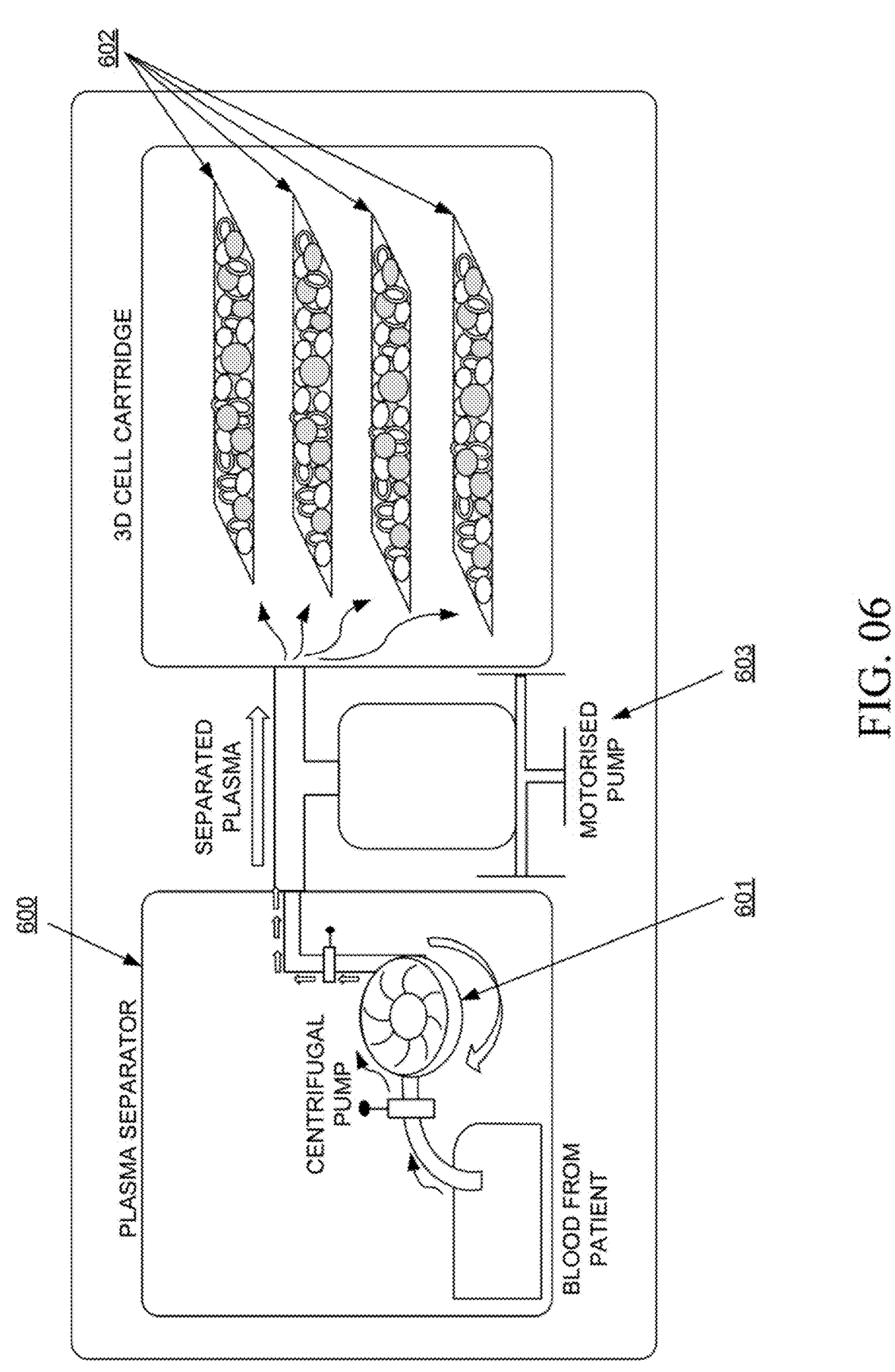
FIG. 6 illustrates the Schematic of the working principle of the device according to an embodiment of the present invention.

FIG. 6 illustrates the Schematic of the working principle of the device according to an embodiment of the present invention. Accordingly, the device comprises of an inline plasma separator (600) and one or more 3D cell cartridges (602) with co-cultured cells on either side of a 3D construct. The blood from the patient is drawn using a centrifugal pump (601) and subjected to separation of plasma or the de-cellularised blood and the separated plasma or the de-cellularised blood is pumped (603) into the 3D cell cartridge (602) for removing lipophilic albumin-bound substances from the plasma or the de-cellularised blood thereby allowing the damaged liver to regenerate by reducing the metabolic burden. The 3D cell cartridge (602) herein comprises of microfluidic chamber with the similar network as found in the human liver and the 3D cell cartridge (602) has flow circuits for plasma/de-cellularised blood where the flow circuits are lined by a coculture of cells. The array of cells in the chamber serves as a miniature liver and which multiple such arrays will be stacked to achieve a significant hepatic function.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments.

H) ADVANTAGES OF THE INVENTION

The proposed invention provides bioengineered artificial functional liver which can be connected to a patient suffering from acute liver failure.

The proposed invention uses a 3D cell cartridge which will use biologically and metabolically active cells.

The proposed invention provides the development of an in-line plasma separator.

The proposed invention provides a method of tissue culture wherein the multiple type of cells are cultured on a single membrane in a particular arrangement.

The proposed invention will provide necessary support to the patient suffering from acute liver failure and will facilitate the regeneration of the native liver.

I claim:

1. A bioartificial liver device for removing lipophilic albumin-bound substances including bilirubin, bile acids, medium chain fatty acids, metabolites of aromatic amino acids, and cytokines from a patient's blood, the bioartificial liver device comprising:

an inline plasma separator; and one or more 3D cell cartridges with co-cultured liver cells including biologically active patient derived hepatocytes cells and endothelial cells, wherein each 3D cell cartridge comprises a membrane having a first surface and a second surface opposite to the first surface such that the biologically active patient derived hepatocytes cells are cultured on the first surface and the biologically active endothelial cells are cultured on the second surface, wherein a ratio of a cell number cultured in each 3D cell cartridge is at least 2:1 (patient derived hepatocytes cells:endothelial cells), wherein, the blood from the patient is drawn using a centrifugal pump and subjected to separation of plasma in the inline plasma separator and the plasma separated from the inline plasma separator is pumped into the one or more 3D cell cartridges for removing lipophilic albumin-bound substances from the plasma thereby allowing a damaged liver to regenerate by reducing a metabolic burden.

2. The bioartificial liver device as claimed in claim 1, wherein each 3D cell cartridge comprises of a microfluidic chamber with a similar network as found in a human liver.

3. The bioartificial liver device as claimed in claim 2, wherein the microfluidic chamber in each 3D cell cartridge has flow circuits for the plasma where the flow circuits are lined by a coculture of the biologically active patient derived hepatocytes cells, the endothelial cells and fibroblasts.

4. The bioartificial liver device as claimed in claim 2, wherein each 3D cell cartridge comprises an array of cells in the microfluidic chamber serving as a miniature liver and which multiple such arrays are stacked to achieve a hepatic function.

5. The bioartificial liver device as claimed in claim 1, wherein the biologically active hepatocytes cells and endothelial cells are cultured on a single membrane.

* * * * *